United States Patent
Ide et al.

(10) Patent No.: US 11,951,463 B2
(45) Date of Patent: Apr. 9, 2024

(54) CATALYST COMPOSITIONS AND THEIR USE IN AROMATIC ALKYLATION PROCESSES

(71) Applicant: ExxonMobil Chemical Patents Inc., Baytown, TX (US)

(72) Inventors: Matthew S. Ide, Doylestown, PA (US); Brett T. Loveless, Houston, TX (US); Doron Levin, Highland Park, NJ (US); William W. Lonergan, Humble, TX (US); Matthew J. Vincent, Kingwood, TX (US); Wei-Ping Tai, Yardley, PA (US); Federico Barrai, Houston, TX (US)

(73) Assignee: ExxonMobil Engineering & Technology Company, Baytown, TX (US)

( * ) Notice: Subject to any disclaimer, the term of this patent is extended or adjusted under 35 U.S.C. 154(b) by 0 days.

(21) Appl. No.: 16/497,239

(22) PCT Filed: Mar. 19, 2018

(86) PCT No.: PCT/US2018/023077
§ 371 (c)(1),
(2) Date: Sep. 24, 2019

(87) PCT Pub. No.: WO2018/183009
PCT Pub. Date: Oct. 4, 2018

(65) Prior Publication Data
US 2020/0376471 A1 Dec. 3, 2020

Related U.S. Application Data

(60) Provisional application No. 62/478,340, filed on Mar. 29, 2017, provisional application No. 62/478,237, filed on Mar. 29, 2017.

(30) Foreign Application Priority Data

Jun. 2, 2017 (EP) .................................... 17174273

(51) Int. Cl.
*B01J 35/02* (2006.01)
*B01J 29/08* (2006.01)
(Continued)

(52) U.S. Cl.
CPC ........... *B01J 29/7038* (2013.01); *B01J 29/08* (2013.01); *B01J 29/18* (2013.01); *B01J 29/70* (2013.01);
(Continued)

(58) Field of Classification Search
None
See application file for complete search history.

(56) References Cited

U.S. PATENT DOCUMENTS 4,367,164 A * 1/1983 Shiroto .................... B01J 35/10
502/84
4,891,458 A 1/1990 Innes et al.
(Continued)

FOREIGN PATENT DOCUMENTS

WO 98/07673 A 2/1998
WO WO2004/071999 8/2004
(Continued)

OTHER PUBLICATIONS

Sasol "Product Information Silica Aluminas, SIRAL"2014 http://www.sasoltechdata.com/tds/SIRAL.pdf (Year: 2014).*
(Continued)

*Primary Examiner* — In Suk C Bullock
*Assistant Examiner* — Alyssa L Cepluch (57) ABSTRACT

Catalyst compositions comprising a zeolite and a mesoporous support or binder are disclosed. The mesoporous
(Continued)

support or binder comprises a mesoporous metal oxide having a particle diameter of greater than or equal to 20 μm at 50% of the cumulative pore size distribution ($d_{50}$). Also disclosed are processes for producing a mono-alkylated aromatic compound (e.g., ethylbenzene or cumene) which exhibit improved yield of the mono-alkylated aromatic compound using alkylation catalysts comprising one or more of these catalyst compositions.

23 Claims, 1 Drawing Sheet

(51) Int. Cl.
  *B01J 29/18* (2006.01)
  *B01J 29/70* (2006.01)
  *B01J 35/10* (2006.01)
  *C07C 2/66* (2006.01)

(52) U.S. Cl.
  CPC ......... *B01J 29/7007* (2013.01); *B01J 35/023* (2013.01); *B01J 35/1019* (2013.01); *B01J 35/1038* (2013.01); *B01J 35/1042* (2013.01); *B01J 35/1071* (2013.01); *C07C 2/66* (2013.01); *C07C 2529/70* (2013.01)

(56) References Cited

U.S. PATENT DOCUMENTS

| | | | |
|---|---|---|---|
| 4,992,606 | A | 2/1991 | Kushnerick et al. |
| 5,242,676 | A * | 9/1993 | Apelian ............... C07D 201/04 502/64 |
| 5,288,927 | A * | 2/1994 | Chang .................... C07C 37/14 568/784 |
| 5,334,795 | A | 8/1994 | Chu et al. |
| 5,409,595 | A * | 4/1995 | Harandi ................ C10G 45/64 585/419 |
| 5,942,650 | A | 8/1999 | Gajda |
| 6,090,991 | A | 7/2000 | Butler et al. |
| 7,019,185 | B2 * | 3/2006 | Dandekar ............... C07C 2/66 585/446 |
| 7,425,659 | B2 | 9/2008 | Clark |
| 7,645,913 | B2 | 1/2010 | Clark et al. |
| 8,022,261 | B2 | 9/2011 | Kalyanaraman et al. |
| 8,247,629 | B2 | 8/2012 | Clark et al. |
| 8,840,779 | B2 | 9/2014 | McCarthy et al. |
| 9,944,865 | B2 | 4/2018 | Ide et al. |
| 2002/0042548 | A1 | 4/2002 | Dandekar et al. |
| 2002/0049133 | A1 * | 4/2002 | Ziebarth ................. B01J 29/40 502/67 |
| 2004/0027256 | A1 * | 2/2004 | Lane ......................... G08B 6/00 340/945 |
| 2004/0138051 | A1 | 7/2004 | Shan et al. |
| 2006/0224031 | A1 * | 10/2006 | Jan .......................... C07C 6/126 585/467 |
| 2007/0042905 | A1 | 2/2007 | Negiz et al. |
| 2008/0177120 | A1 | 7/2008 | Clark et al. |
| 2008/0319242 | A1 | 12/2008 | Clark et al. |
| 2011/0079145 | A1 | 4/2011 | Dolan et al. |
| 2011/0218356 | A1 * | 9/2011 | Ditzel ...................... B01J 29/18 560/232 |
| 2012/0083635 | A1 | 4/2012 | Boldingh et al. |
| 2012/0088937 | A1 | 4/2012 | Jan et al. |
| 2013/0137910 | A1 | 5/2013 | Vincent et al. |
| 2015/0231618 | A1 * | 8/2015 | Mao ......................... B01J 23/85 502/66 |
| 2016/0220987 | A1 * | 8/2016 | Lai ........................... B01J 29/67 |

FOREIGN PATENT DOCUMENTS

| | | |
|---|---|---|
| WO | WO2014/076625 | 5/2014 |
| WO | 2014/182294 A | 11/2014 |
| WO | 2018/183012 A | 10/2018 |

OTHER PUBLICATIONS

Sasol "Pural Catapal High-Purity Alumina Hydrates" Brochure. pp. 1-16. retrieved Jul. 22, 2022 (Year: 2022).*
Rouquerol, J. et al. "International union of pure and applied chemistry physical chemistry division, commission on colloid and surface chemistry, Subcommittee on characterization of porous solids- recommendations for the characterization of porous solids", Pure and Appl. Chem., vol. 66, No. 8, pp. 1739-1758, Jan. 1, 1994.
UOP: "UOP Versal Alumina: A family of High Performance Powders", Apr. 1, 2012. URL:http://www.uop.com/?document=uop-versal-alumina-brochure&download=1.
Sasol: "Sasol Germany GmbH", Jan. 1, 2003, URL:http://www.sasoltechdata.com/tds/PURALCATAPAL.pdf.
De Araujo, L. R. R. et al, H3PO4/Al2O3 catalysts: characterizatioin and catalytic evaluation of oleic acid conversion to biofuels and biolubricant. *Materials Research*, Jun. 30, 2006, vol. 9, No. 2, pp. 181-184.

* cited by examiner

US 11,951,463 B2

CATALYST COMPOSITIONS AND THEIR USE IN AROMATIC ALKYLATION PROCESSES

This application is a National Phase Application of PCT Application Serial No. PCT/US2018/023077, filed Mar. 19, 2018, which claims the benefits of and priorities to U.S. Provisional Application No. 62/478,237, entitled "CATALYST COMPOSITIONS AND THEIR USE IN AROMATIC ALKYLATION PROCESSES", filed on Mar. 29, 2017 and EP application 17174273.7, filed on Jun. 2, 2017, and U.S. Provisional Application No. 62/478,340, entitled "METHODS FOR REMOVING IMPURITIES FROM A HYDROCARBON STREAM AND THEIR USE IN AROMATIC ALKYLATION PROCESSES", filed on Mar. 29, 2017, the disclosures of which are incorporated herein by their reference in their entireties.

FIELD OF THE INVENTION

This invention relates to catalyst compositions and their use in alkylation catalysts deployed in aromatic alkylation processes to achieve improved yield of the desirable mono-alkylated aromatic compound. Particularly, this invention relates to alkylation catalysts and their use is the alkylation of benzene with ethylene or propylene, to achieve improved yields of mono-alkylated aromatic compounds, such as ethylbenzene and cumene.

BACKGROUND OF THE INVENTION

Ethylbenzene is a valuable commodity chemical and is used in the production of styrene monomer. Cumene (isopropylbenzene) is also a valuable commodity chemical and is used in the production of phenol and acetone.

Presently, ethylbenzene is often produced by a liquid phase aromatic alkylation process from benzene and ethylene in the presence of an alkylation catalyst. The liquid phase process operates at a lower temperature than its vapor phase counterpart. One advantage of the liquid phase alkylation is a lower yield of undesired by-products, poly-alkylated aromatic compound(s). The alkylation of aromatic hydrocarbon compounds employing zeolite-based alkylation catalysts is known and understood in the art. U.S. Pat. No. 5,334,795 describes the liquid phase alkylation of benzene with ethylene in the presence of MCM-22 to produce ethylbenzene; and U.S. Pat. No. 4,891,458 discloses liquid phase alkylation and transalkylation processes using zeolite beta.

Cumene is often produced by a liquid phase aromatic alkylation process from benzene and propylene in the presence of a zeolite-based alkylation catalyst. U.S. Pat. No. 4,992,606 discloses a process for preparing cumene using MCM-22 in liquid phase.

Typically, these zeolite-based alkylation catalysts include a catalyst composition comprised of a zeolite component and a mesoporous support or mesoporous binder, such as a mesoporous alumina binder.

Despite the advances in the liquid phase aromatic alkylation processes, there is a need for an improved aromatic alkylation process which has a higher yield of the desired mono-alkylated aromatic compound, such as ethylbenzene or cumene, and with lower production of the undesirable byproduct poly-alkylated aromatic compounds, such as di-ethylbenzene or di-isopropylbenzene.

SUMMARY OF THE INVENTION

It has now been found that an alkylation catalyst which comprises any one of the catalyst compositions of this invention meets this need for a higher yield of (and improved mono-selectivity to) the desired mono-alkylated aromatic compounds when deployed in aromatic alkylation processes. These catalyst compositions are comprised of a suitable zeolite and a mesoporous support which comprises a mesoporous metal oxide. Improved mono-selectivity is achieved by increasing the particle diameter (e.g., the particle diameter at 50% of the cumulative pore size distribution, $d_{50}$) of the mesoporous metal oxide. The increased particle diameter thereby decreases the total surface area of the catalyst composition and, in turn, reduces the diffusion limitations of the alkylation catalyst.

In a first aspect, this invention is a catalyst composition which comprises a zeolite and a mesoporous support or mesoporous binder. The mesoporous support or mesoporous binder comprises a mesoporous metal oxide having a particle diameter at 50% of the cumulative pore size distribution ($d_{50}$) of greater than or equal to 20 μm.

Advantageously, the zeolite has a framework structure which comprises BEA*, FAU, MOR, MWW and mixtures of two or more thereof. The framework structure which comprises BEA* is zeolite beta. The framework structure which comprises FAU is faujasite, zeolite Y, USY, Deal-Y, UHP-Y and REY, The framework structure which comprises MOR is mordenite, TEA-mordenite, EMM-34 and UZM-14. The framework structure which comprises MWW is a MCM-22 family material, as defined herein.

Advantageously, the mesoporous metal oxide includes, but is not limited to, any one of aluminum oxide, aluminum hydroxide, boehmite, pseudoboehmite alumina, amorphous silica-alumina or combinations of two or more thereof. The alumina content of said mesoporous metal oxide is greater than or equal to 75, or in the range of from 75 to 95, in one or more embodiments. Preferably, the mesoporous metal oxide has a pore volume of less than 1 cc/g.

Advantageously, the catalyst composition has a surface area of less than or equal to 300 m²/g. In one or more embodiments, the zeolite has a Si/Al$_2$ molar ratio of less than or equal to 50. In other embodiments, the ratio of the zeolite to the mesoporous metal oxide in the catalyst composition is in the range of from 1:99 to 100:90 by weight, typically 80:20 or 65:35 by weight.

In a second aspect, the invention is a process for producing a mono-alkylated aromatic compound. In step (a) of the process, a portion of a stream comprising an alkylatable aromatic compound is contacted with a stream comprising an alkylating agent in the presence of an alkylation catalyst under alkylation conditions to produce an alkylation effluent. The alkylation effluent comprises mono-alkylated aromatic compound and said poly-alkylated aromatic compound. The alkylation catalyst deployed in the process comprises any one of the catalyst compositions of this invention.

Advantageously, the catalyst composition of this invention may be deployed in a catalyst system as a method to improve the overall selectivity of a fixed-bed mono-alkylated aromatic compound process while maintaining complete conversion of the olefin reactant and optionally, alkylate aromatic compound. In the catalyst system, any one of the inventive catalyst compositions is deployed in the catalyst bed along with one or more different catalyst compositions. Alternatively, the two catalyst compositions may be deployed in two or more catalysts beds which are in fluid communication with each other. In one or more embodiments, the first catalyst composition deployed is more selective for the production of the desirable mono-alkylated aromatic compound (and produces less of the undersirable poly-alkylated aromatic compound by-products) in an aromatic alkylation process, but it has a lower catalytic activity. The second catalyst composition has a higher catalytic activity in the aromatic alkylation process, but it exhibits a lower selectivity for the production of the desirable mono-alkylated aromatic compound (and produces more of the undesirable poly-alkylated aromatic compound by-products).

Advantageously, in a further step (b) of the process, the alkylation effluent may be separated to recover a stream comprising the mono-alkylated aromatic compound and a stream comprising a polyalkylated aromatic compound.

Advantageously, in a further step (c) of the process, the stream comprising the poly-alkylated aromatic compound is contacted with another portion of the stream comprising the alkylatable aromatic compound in the presence of a transalkylation catalyst under transalkylation conditions to produce a transalkylation effluent which comprises additional mono-alkylated aromatic compound. The transalkylation catalyst is a large pore molecular sieve, preferably a large pore zeolite having a Constraint Index of less than 2, or it may be a MCM-22 family material, as defined herein.

In one or more embodiments, the stream comprising the alkylatable aromatic compound is an impure stream which further comprises impurities, as defined herein. Advantageously, the process further comprises a guard bed zone to remove such impurities via adsorption. The process further includes additional steps. In step (d), the impure stream is supplied to a guard bed zone where a guard bed material is disposed therein. Then in step (e), the impure stream is contacted with the guard bed material under treatment conditions to remove at least a portion of said impurities to produce a treated stream comprising an alkylatable aromatic compound having a reduced amount of impurities.

Advantageously, the process further comprises a guard bed zone to remove such impurities via adsorption but in the presence of an alkylating agent to produce additional mono-alkylated aromatic compound at the same time. The process further includes additional steps. In step (f), an alkylating agent is supplied along with the impure stream to said guard bed zone having said guard bed material disposed therein. Then, in step (g), the impure stream is contacted with the alkylating agent in the presence of the guard bed material under treatment conditions to remove at least a portion of said impurities. At the same time, at least a portion of the alkylatable aromatic compound is alkylated with the alkylating agent. A treated stream is produced which has a reduced amount of impurities and comprises an alkylatable aromatic compound and additional mono-alkylated aromatic compound.

Advantageously, the guard bed material includes, and may be selected from the group consisting of a clay, a resin, an activated alumina, a molecular sieve and mixtures of two or more thereof.

In one or more embodiments, the alkylatable aromatic compound is benzene. In such embodiments, when the alkylating agent is ethylene, the mono-alkylated aromatic compound is ethylbenzene and the poly-alkylated aromatic compound is poly-ethylbenzene. In such embodiments, when the alkylating agent is propylene, the mono-alkylated aromatic compound is cumene and the poly-alkylated aromatic compound is poly-isopropylbenzene.

DETAILED DESCRIPTION OF THE INVENTION

A higher yield of the desired mono-alkylated aromatic compounds is exhibited by alkylation catalysts which are comprised of any one of the catalyst compositions of this invention, when such catalysts are deployed in processes for producing a mono-alkylated aromatic compound, preferably ethylbenzene or cumene.

Definitions

The term "activated alumina", as used herein, means a granular, highly porous form of aluminum oxide for use for adsorption.

The term "alkylation catalyst", as used herein, means a catalyst for use in aromatic alkylation processes which comprises any one of the catalyst compositions of this invention The term "alkylatable aromatic compound", as used herein, means an aromatic compound that may receive an alkyl group. One non-limiting example of an alkylatable aromatic compound is benzene.

The term "alkylating agent", as used herein, means a compound which may donate an alkyl group to an alkylatable aromatic compound. Non-limiting examples of an alkylating agent are ethylene, propylene, and butylene. Another non-limiting example is any poly-alkylated aromatic compound that is capable of donating an alkyl group to an alkylatable aromatic compound.

The term "aromatic", as used herein, in reference to the alkylatable aromatic compounds which are useful herein, is to be understood in accordance with its art-recognized scope which includes substituted and unsubstituted mono- and polynuclear compounds. Compounds of an aromatic character which possess a heteroatom (e.g., N or S) are also useful provided they do not act as catalyst poisons, as defined below, under the reaction conditions selected.

The term "at least partially liquid phase", as used herein, means a mixture having at least 1 wt. % liquid phase, optionally at least 5 wt. % liquid phase, at a given temperature, pressure, and composition.

The term "catalyst poisons", as used herein, means one or more impurities, defined herein, which acts to reduce the cycle-length of a molecular sieve or zeolite.

The term "Constraint Index", as used herein, is defined in U.S. Pat. Nos. 3,972,832 and 4,016,218.

The term "cumulative pore size distribution ($d_{50}$)", as used herein, means the median value of the particle size distribution in a sample where the value of the particle diameter is at 50% of the cumulative distribution. For example, if $d_{50=20}$ µm for a sample, then 50% of the particles in the sample are larger than 20 µm, and 50% smaller than 20 µm.

The term "pore volume", as used herein, means the volume of the pores in a material as measured by mercury intrusion as measure by ASTM method D4284, and it is expressed as cc/g.

The term "guard bed material", as used herein, includes a material that can act to increase the rate constant in a chemical reaction, as well as a material that can act to adsorb catalyst poisons from a hydrocarbon stream.

The terms "cumulative pore size distribution ($d_{50}$)" and "cumulative particle size distribution", as used herein, mean the median value of the particle size distribution in a sample where the value of the particle diameter is at 50% of the cumulative distribution. For example, if $d_{50}=20$ μm for a sample, then 50% of the particles in the sample are larger than 20 μm, and 50% smaller than 20 μm.

Zeolite beta has a *BEA framework type and is described in U.S. Pat. No. 3,308,069 and U.S. Reissue Pat. No. 28,341.

Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104. EMM-34, also referred to as meso-mordenite, is a zeolite synthesized from structure directing agents TEA (tetraethyl ammonium cation) or MTEA (methyl triethyl ammonium cation) and having a mesopore surface area of greater than 30 $m^2/g$ and comprising agglomerates composed of primary crystallites, wherein the primary crystallites have an average primary crystal size as measured by TEM of less than 80 nm and an aspect ratio of less than 2, as disclosed in International Publication WO2016/126431, incorporated by reference where permitted. UZM-14 is described in U.S. Publication 20090325785 A1. The MOR framework type includes various forms of mordenite such as, for example, TEA-mordenite, EMM-34 and UZM-14.

The term "MCM-22 family material" (or "MCM-22 family molecular sieve"), as used herein, can include:
(i) molecular sieves made from a common first degree crystalline building block "unit cell having the MWW framework topology." A unit cell is a spatial arrangement of atoms which is tiled in three-dimensional space to describe the crystal as described in the "Atlas of Zeolite Framework Types," by Ch. Baerlocher, W. M. Meier and D. H. Olson (Elsevier, 5th Ed., 2001);
(ii) molecular sieves made from a common second degree building block, a 2-dimensional tiling of such MWW framework type unit cells, forming a "monolayer of one unit cell thickness," preferably one c-unit cell thickness;
(iii) molecular sieves made from common second degree building blocks, "layers of one or more than one unit cell thickness", wherein the layer of more than one unit cell thickness is made from stacking, packing, or binding at least two monolayers of one unit cell thick of unit cells having the MWW framework topology. The stacking of such second degree building blocks can be in a regular fashion, an irregular fashion, a random fashion, and any combination thereof; or
(iv) molecular sieves made by any regular or random 2-dimensional or 3-dimensional combination of unit cells having the MWW framework topology.

The MCM-22 family materials are characterized by having an X-ray diffraction pattern including d-spacing maxima at 12.4±0.25, 3.57±0.07 and 3.42±0.07 Angstroms (either calcined or as-synthesized). The MCM-22 family materials may also be characterized by having an X-ray diffraction pattern including d-spacing maxima at 12.4±0.25, 6.9±0.15, 3.57±0.07 and 3.42±0.07 Angstroms (either calcined or as-synthesized). The X-ray diffraction data used to characterize the molecular sieve are obtained by standard techniques using the K-alpha doublet of copper as the incident radiation and a diffractometer equipped with a scintillation counter and associated computer as the collection system.

Members of the MCM-22 family include, but are not limited to, MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent 0293032), ITQ-1 (described in U.S. Pat. No. 6,077,498), ITQ-2 (described in InternatPatentnal Patent Publication No. WO97/17290), ITQ-30 (described in International Patent Publication No. WO2005118476), MCM-36 (described in U.S. Pat. No. 5,250,277), MCM-49 (described in U.S. Pat. No. 5,236,575), MCM-56 (described in U.S. Pat. No. 5,362,697; and an EMM-10 family molecular sieve (described or characterized in U.S. Pat. Nos. 7,959,899 and 8,110,176; and U.S. Patent Application Publication No. 2008/0045768), such as EMM-10, EMM-10-P, EMM-12 and EMM-13. Typically, the molecular sieve of the MCM-22 family is in the hydrogen form and having hydrogen ions, for example, acidic.

Related zeolites to be included in the MCM-22 family are UZM-8 (described in U.S. Pat. No. 6,756,030), UZM-8HS (described in U.S. Pat. No. 7,713,513), UZM-37 (described in U.S. Pat. No. 8,158,105), and MIT-1 is described in Chem. Sci., 2015, 6, 6320-6324, all of which are also suitable for use as the molecular sieve of the MCM-22 family.

The term "hydrocarbon", as used herein, means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n, where n is the number of carbon atom(s) per molecule.

The term "mono-alkylated aromatic compound", as used herein, means an aromatic compound that has only one alkyl substituent. Non-limiting examples of mono-alkylated aromatic compounds are ethylbenzene, iso-propylbenzene (cumene) and sec-butylbenzene.

The term "poly-alkylated aromatic compound", as used herein, means an aromatic compound that has more than one alkyl substituent. A non-limiting example of a poly-alkylated aromatic compound is poly-ethylbenzene, e.g., di-ethylbenzene, tri-ethylbenzene, and poly-isopropylbenzene, e.g., di-isopropylbenzene, and tri-isopropylbenzene.

The term "impurities" as used herein, includes, but is not limited to, compounds having at least one of the following elements: nitrogen, halogens, oxygen, sulfur, arsenic, selenium, tellurium, phosphorus, and Group 1 through Group 12 metals.

The term "large pore molecular sieve", as used herein, means molecular sieve preferably having a Constraint Index of less than 2.

Suitable large pore molecular sieves include the aforementioned zeolite beta and mordenite as well as faujasite, including zeolite Y, Ultrastable Y (USY), Dealuminized Y (Deal Y), Ultrahydrophobic Y (UHP-Y), Rare earth exchanged Y (REY). Also included is ZSM-2, ZSM-3, ZSM-4, ZSM-12, ZSM-14, ZSM-18, ZSM-20, ZSM-50, MCM-68, ECR-4, ECR-17, ECR-32, ECR-35 and mixtures of two or more thereof.

Zeolite Y is described in U.S. Pat. No. 3,130,007. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Ultrahydrophobic Y (UHP-Y) is described in U.S. Pat. No. 4,401,556. Rare earth exchanged Y (REY) is described in U.S. Pat. No. 3,524,820.

Zeolite ZSM-2 is described in U.S. Pat. No. 3,411,874. Zeolite ZSM-3 is described in U.S. Pat. No. 3,415,736. ZSM-4 is described in U.S. Pat. No. 4,021,447. ZSM-12 is described in U.S. Pat. No. 3,832,449. ZSM-14 is described in U.S. Pat. No. 3,923,636. ZSM-18 is described in U.S. Pat. No. 3,950,496. Zeolite ZSM-20 is described in U.S. Pat. No.

3,972,983. ZSM-50 is described in U.S. Pat. No. 4,640,829. MCM-68 is described in U.S. Pat. No. 6,049,018. ECR-4 is described in U.S. Pat. No. 4,965,059. ECR-17 is described in EP Publication EP0259526. ECR-32 is described in U.S. Pat. No. 4,931,267. ECR-35 is described in U.S. Pat. No. 5,116,590.

The term "surface area", as used herein, means the surface area of a material or catalyst composition as determined by mercury intrusion tests performed in accordance with ASTM method D4284.

The term mesoporous, as used herein, means a material containing pores with diameters between 2 and 50 nm.

The term "normalized", as used herein, with respect to a series of numerical values, means to scale each value by a common factor for purposes of comparison. The normalized value for the common factor will equal 1.

The term "comprising" (and its grammatical variations), as used herein, is used in the inclusive sense of "having" or "including" and not in the exclusive sense of "consisting only of." The terms "a" and "the", as used herein, are understood to encompass the plural as well as the singular.

The entire contents of each and every aforementioned patents and publications are incorporated herein by reference in their entireties.

Catalyst Composition

In a first aspect, this invention is a catalyst composition which comprises a zeolite and a mesoporous support or mesoporous binder. The mesoporous support or mesoporous binder comprises a mesoporous metal oxide having a particle diameter of greater than or equal to 20 µm at 50% of the cumulative pore size distribution ($d_{50}$). The pore volume of the mesoporous metal oxide is less than 1 cc/g in one or more embodiments.

In one or more embodiments, the zeolite has a Constraint Index of less than 3, preferably less than 2, most preferably, less than 1. The zeolite which has a Constraint Index of less than 3 includes, but is not limited to, a zeolite having the framework structure which comprises BEA*, FAU, MOR, MWW and mixtures of two or more thereof. The BEA* framework structure comprises zeolite beta. The FAU framework structure comprises faujasite, zeolite Y, USY, Deal-Y, UHP-Y and REY, and a mixture of two or more thereof. The MOR framework structure comprises mordenite, TEA-mordenite, EMM-34 (meso-mordenite) and UZM-14, and a mixture of two or more thereof. The MWW framework structure comprises any one of the MCM-22 family material, as defined herein, and a mixture of two or more thereof. Other zeolites having a Constraint Index of less than 3 include, but are not limited to, ZSM-4, ZSM-12, ZSM-20, ZSM-50 and MCM-68. Mixtures of these zeolites which have a Constraint Index of less than 3 are contemplated. The preferred zeolite is a MCM-22 family material, including, but not limited to MCM-22, MCM-49 or MCM-56.

The $Si/Al_2$ molar ratio of the zeolite is less than or equal to 50, or less than or equal to 100, or in the range of from 10 to 50, or in the range of from 10 to 100.

The mesoporous metal oxide has a particle diameter of greater than or equal to 20 µm at 50% of the cumulative pore size distribution ($d_{50}$). Such $d_{50}$ particle diameter may be greater than or equal to 25 µm, or greater than or equal to 35 µm, or greater than or equal to 50 µm at 50% of the cumulative pore size distribution ($d_{50}$. The $d_{50}$ particle diameter may be in the range from 20 µm up to 60 µm, or in the preferred range of from 25 µm to 50 µm.

The pore volume of the mesoporous metal oxide is less than 1 cc/g, or less than or equal to 0.75, or less than or equal to 0.5, or in the preferred range of 0.45 to 0.75 cc/g.

The mesoporous metal oxide includes, but is not limited to, any one of aluminum hydroxide, boehmite, pseudoboehmite alumina, aluminum oxide, amorphous silica-alumina and mixtures of two or more thereof. The preferred mesoporous oxide is pseudoboehmite alumina or an amorphous, precipitated silica-alumina.

The alumina content of said mesoporous metal oxide is greater than or equal to 75% or in the range of from 75% to 95%, by weight in one or more embodiments.

The catalyst composition has a surface area of less than or equal to 300 $m^2/g$, or 275 $m^2/g$, or 250 $m^2/g$, or 225 $m^2/g$ in one or more embodiments.

The zeolite has a $Si/Al_2$ molar ratio of less than or equal to 50, or less than or equal to 100, or in the range of from 10 to 50, or in the range of from 10 to 100 in one or more embodiments.

The catalyst composition has a normalized critical pore diameter of less than 1 µm or in the range from 0.4 to 0.9 µm in one or more embodiments.

The ratio of the zeolite to the mesoporous metal oxide is in the range of from 1:99 to 100:0, or in the range from 95:5 to 5:95, or in the range from 90:10 to 10:90, or in the range from 80:20 to 10:90, or in the range from 65:35 to 35:65, by weight.

Not to be bound by any theory, it is believed that the lower surface area and larger particle size of the mesoporous metal oxides used in the catalyst compositions of this invention may create a more open pore network thereby providing greater accessibility to the strong acid sites on the exterior and the interior of the zeolite of the catalyst composition, as compared to smaller particle, higher surface area mesoporous metal oxides.

The method of making the composition is not particularly limited. It may be made by any suitable method known in the art for combing a zeolite and a mesoporous metal oxide, such as for example via co-extrusion. That is the zeolite and the mesoporous metal oxide may be co-extruded to form one or more of the catalyst compositions of this invention.

Process for Producing Mono-Alkylated Aromatic Compounds

In a second aspect, the invention is a process for producing a mono-alkylated aromatic compound. In step (a) of the process, a portion of a stream comprising an alkylatable aromatic compound is contacted with a stream comprising an alkylating agent in the presence of an alkylation catalyst under alkylation conditions to produce an alkylation effluent. The alkylation effluent comprises mono-alkylated aromatic compound and said poly-alkylated aromatic compound.

The alkylation catalyst deployed in the process comprises any one of the catalyst compositions of this invention. Further, such alkylation catalyst is the same or different from the guard bed material, discussed below.

In one or more embodiments, the alkylation catalyst further comprises a second catalyst composition, wherein said second catalyst composition comprises another zeolite and another mesoporous binder. Such another mesoporous binder of the second catalyst composition is different from the mesoporous binder of the first catalyst composition. In one or more embodiments, the first catalyst composition has a selectivity to said mono-alkylated aromatic greater than said selectivity of said second catalyst composition. In addition or optionally, the first catalyst composition has a catalytic activity that is less than said catalytic activity of said second catalyst composition.

In one or more embodiments, the zeolite of said first catalyst composition is the same or different from the zeolite of said second catalyst composition. The zeolite of the second catalyst composition has a framework structure which comprises BEA*, FAU, MOR, MWW and mixtures of two or more thereof.

In one or more embodiments, the zeolite of the second catalyst composition can be combined in conventional manner with an oxide binder, such as alumina or silica, such that the final second catalyst composition contains between 1 and 100 wt. % of the zeolite.

The alkylating agent, defined below, is typically an olefin, preferably ethylene or propylene.

In a further step (b) of the process, the alkylation effluent may be separated to recover a stream comprising the mono-alkylated aromatic compound and a stream comprising a polyalkylated aromatic compound.

Additional mono-alkylated aromatic compound may be produced from the poly-alkylated aromatic compounds stream via transalkylation. In a further step (c) of the process, the stream comprising the poly-alkylated aromatic compound is contacted with another portion of the stream comprising the alkylatable aromatic compound, benzene for example, in the presence of a transalkylation catalyst under transalkylation conditions to produce a transalkylation effluent which comprises additional mono-alkylated aromatic compound. The transalkylation catalyst is a large pore molecular sieve, as defined herein. Preferably, the transalkylation catalyst is a large pore zeolite having a Constraint Index of less than 2. Alternatively, the transalkylation catalyst may be a MCM-22 family material, as defined herein.

The catalyst composition of this invention may be deployed in a catalyst system as a method to improve the overall selectivity of a fixed-bed mono-alkylated aromatic compound process, for example, an ethylbenzene or cumene process, while maintaining complete conversion of the olefin reactant and optionally, alkylate aromatic compound. In the catalyst system, any one of the inventive catalyst compositions is deployed in the catalyst bed along with one or more different catalyst compositions. Alternatively, the two catalyst compositions may be deployed in two or more catalysts beds which are in fluid communication with each other.

In one or more embodiments, the first catalyst composition deployed is more selective for the production of the desirable mono-alkylated aromatic compound (and produces less of the undersirable poly-alkylated aromatic compound by-products) in an aromatic alkylation process, but it has a lower catalytic activity. The second catalyst composition has a higher catalytic activity in the aromatic alkylation process, but it exhibits a lower selectivity for the production of the desirable mono-alkylated aromatic compound (and produces more of the undesirable poly-alkylated aromatic compound by-products).

In another embodiment, the process using this catalyst system includes a first catalyst composition that is contacted with an olefin (e.g., ethylene or propylene) and an alkylatable aromatic compound (e.g., benzene) to form an effluent which comprises both mono-alkylated (e/g., ethylbenzene or cumene) and poly-alkylated aromatic compounds (e.g., di-ethylbenzene or di-isopropylbenzene) and unreacted olefin and alkylatable aromatic compounds. This effluent is then contacted with the second catalyst composition to achieve at least 99% conversion of the olefin while producing additional mono-alkylated and poly-alkylated aromatic compounds and unreacted aromatic compound.

One embodiment is a process for the production of cumene from propylene and benzene in a fixed-bed reactor using the catalyst system. Such catalyst system would employ a first and a second catalyst composition. The first catalyst (more-selective) composition may be one or more of the catalyst compositions of this disclosure, such as for example, inventive Examples 7 to 11, discussed below. The second catalyst composition is different from the first catalyst composition and may be, for example, comparative Example 4, discussed below.

Using the first catalyst composition alone, there is at least a 99% conversion of the propylene at approximately 82% of the fixed-bed at a weight-hourly space velocity of 1 (WHSV=1 hr-1). When using this first catalyst alone and additional production capacity is desired, then the WHSV would have to be increased; however, incomplete conversion would be achieved at a WHSV greater than 1.22 $hr^{-1}$.

When the second catalyst composition is used alone, there is at least a 99% conversion of the propylene at approximately 40% of the fixed-bed at a weight-hourly space velocity of 1 (WHSV=1 hr-1). When using this second catalyst alone and additional production capacity is desired, then the WHSV could be increased to a WHSV of up to 2.5 $hr^{-1}$ to maintain a 99% conversion.

In order to operate at a higher WHSV with improved selectivity, then the catalyst system of the two catalysts above enables a solution. A catalyst bed is constructed that contains a portion, such as for example, 50% by weight, of a first catalyst composition, which is or may be one of the catalyst compositions of this disclosure. The catalyst bed also contains a portion, such as for example, 50% by weight, of the second catalyst composition which is different from the first catalyst composition. In the process, the more selective, first catalyst composition is contacted first by the propylene and benzene feed. The more active, composition catalyst is then contacted by the effluent of the first catalyst. The advantage of the invention is that a selectivity improvement to desirable mono-alkylated aromatic compound, cumene, is enjoyed at substantially higher production rates (as measured by WHSV) may be achieved than using either catalyst composition alone.

In one or more embodiments, the stream comprising the alkylatable aromatic compound is an impure stream which further comprises impurities, as defined herein. These impurities act as catalyst poisons to the downstream alkylation and transalkylation catalyst, and reduce their cycle length. These catalyst poisons reduce the activity and conversion of these catalysts so that there is a reduced amount of reactants which are converted to products. When the conversion has reduced to a low level, the catalysts must be removed for regeneration to restore activity, or the catalysts are replaced.

As a result, the alkylation step (a) or the transalkylation step (c), the stream comprising the alkylatable aromatic compound may comprise undesirable impurities. This stream may be first treated to remove at least a portion of the impurities to produce a treated feed stream having a reduced amount of impurities.

To remove these impurities, the process may further comprise a guard bed zone to remove such impurities via adsorption. The process further includes additional steps. In step (d), the impure stream is supplied to a guard bed zone where a guard bed material is disposed therein. No alkylating agent is supplied to the guard bed. Then in step (e), the impure stream is contacted with the guard bed material under treatment conditions to remove at least a portion of said impurities to produce a treated stream comprising an alkylatable aromatic compound having a reduced amount of impurities.

When no alkylating agent is supplied to the guard bed zone, the zone is an adsorption zone and is called a non-reactive guard bed. After contact with the guard bed material, a treated feed stream having a reduced amount of impurities is produced; however, no alkylated aromatic compound, such as additional mono-alkylated and poly-alkylated aromatic compounds, is produced.

When alkylating agent is supplied to the guard bed, however, the zone is a reactive zone and is called a reactive guard bed (RGB). After contact with the guard bed material, a treated feed stream having a reduced amount of impurities is produced along with an additional amount of alkylated aromatic compound is produced.

In the RGB embodiment, the process further comprises a guard bed zone to remove such impurities via adsorption but in the presence of an alkylating agent to produce additional mono-alkylated aromatic compound at the same time. The process further includes additional steps. In step (f), an alkylating agent is supplied along with the impure stream to said guard bed zone having said guard bed material disposed therein. Then, in step (g), the impure stream is contacted with the alkylating agent in the presence of the guard bed material under treatment conditions to remove at least a portion of said impurities. At the same time, at least a portion of the alkylatable aromatic compound is alkylated with the alkylating agent.

A treated stream is produced which has a reduced amount of impurities and comprises an alkylatable aromatic compound and additional mono-alkylated aromatic compound.

The guard bed material may be selected from the group consisting of a clay, a resin, an activated alumina, a molecular sieve and mixtures of two or more thereof.

The molecular sieve of the guard bed includes, and may be selected from the group consisting Linde X, Linde A, zeolite beta, faujasite, zeolite Y, Ultrastable Y (USY), Dealuminized Y (Deal Y), Rare Earth Y (REY), Ultrahydrophobic Y (UHP-Y), mordenite, TEA-mordenite, UZM-14, ZSM-3, ZSM-4, ZSM-12, ZSM-14, ZSM-18, ZSM-20 and combinations thereof.

The guard bed zone may be in a separate vessel or reactor, or it may be the first stage of the alkylation or transalkylation reaction zone. The guard bed zone is upstream from the alkylation reaction zone.

In operation of a process for producing a mono-alkylated aromatic compound, at least a portion of a treated feed stream which comprises an alkylatable aromatic compound, typically benzene, is contacted with an alkylating agent stream which comprises an alkylating agent, typically an olefin such as ethylene or propylene, in the presence of an alkylation catalyst under suitable at least partially liquid phase alkylation conditions. At least a portion of the alkylatable aromatic compound is alkylated with the alkylating agent in the alkylating agent stream to produce an effluent stream which comprises the mono-alkylated aromatic compound and poly-alkylated aromatic compounds. The effluent stream may be separated to recover the mono-alkylated aromatic compound stream, such as an ethylbenzene or cumene stream, and the poly-alkylated aromatic compound for further processing. The poly-alkylated aromatic compound stream may be contacted with another portion of the treated feed stream in the presence of a transalkylation catalyst under suitable at least partially liquid phase transalkylation conditions to produce an effluent stream comprising additional mono-alkylated aromatic compound.

In one or more embodiments, the alkylatable aromatic compound is benzene. In this instance, when the alkylating agent is ethylene, then the mono-alkylated aromatic compound is ethylbenzene and an example of one of the poly-alkylated aromatic compounds is poly-ethylbenzene. However, when the alkylating agent is propylene, then the mono-alkylated aromatic compound is cumene, and an example of one of the poly-alkylated aromatic compounds is poly-isopropylbenzene.

Alkylatable Aromatic Compounds

Suitable alkylatable aromatic hydrocarbons for any one of the embodiments of the processes of this invention include benzene, naphthalene, anthracene, naphthacene, perylene, coronene, and phenanthrene, with benzene being preferred.

Substituted alkylatable aromatic compounds which can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups which do not interfere with the alkylation reaction.

Generally the alkyl groups, which can be present as substituents on the aromatic compound, contain from 1 to about 22 carbon atoms and usually from about 1 to 8 carbon atoms, and most usually from about 1 to 4 carbon atoms.

Suitable alkyl substituted aromatic compounds for any one of the embodiments of this invention include toluene, xylene, isopropylbenzene, normal propylbenzene, alpha-methylnaphthalene, ethylbenzene, cumene, mesitylene, durene, p-cymene, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalene; ethylnaphthalene; 2,3-dimethylanthracene; 9-ethylanthracene; 2-methylanthracene; o-methylanthracene; 9,10-dimethyl phenanthrene; and 3-methyl-phenanthrene. Higher molecular weight alkylaromatic hydrocarbons can also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecyltoluene, etc. Very often alkylate is obtained as a high boiling fraction in which the alkyl group attached to the aromatic nucleus varies in size from about $C_6$ to about $C_{12}$. When cumene or ethylbenzene is the desired product, the present process produces acceptably little by-products such as xylenes. The xylenes made in such instances may be less than about 500 ppm.

Reformate containing substantial quantities of benzene, toluene and/or xylene constitutes a useful feed for the process of this invention.

Alkylating Agents

The alkylating agents, which are useful in one or more embodiments of the processes of this invention, generally include any aliphatic or aromatic organic compound having one or more available alkylating olefinic groups capable of reaction with the alkylatable aromatic compound, preferably with the alkylating group possessing from 1 to 5 carbon atoms, or poly-alkylated aromatics compound(s). Examples of suitable alkylating agents for any one of the embodiments of this invention are olefins such as ethylene, propylene, the butenes, and the pentenes; alcohols (inclusive of monoalcohols, dialcohols, trialcohols, etc.), such as methanol, ethanol, the propanols, the butanols, and the pentanols; aldehydes such as formaldehyde, acetaldehyde, propionaldehyde, butyraldehyde, and n-valeraldehyde; and alkyl halides such as methyl chloride, ethyl chloride, the propyl chlorides, the butyl chlorides, and the pentyl chlorides, and so forth.

Mixtures of light olefins are especially useful as alkylating agents in the alkylation process of this invention. Accordingly, mixtures of ethylene, propylene, butenes, and/or pentenes which are major constituents of a variety of refinery streams, e.g., fuel gas, gas plant off-gas containing ethylene, propylene, etc., naphtha cracker off-gas containing light olefins, refinery FCC propane/propylene streams, etc., are useful alkylating agents herein.

Poly-alkylated aromatic compounds suitable for one or more embodiments of this invention include, but are not limited to, polyethylbenzene(s), polyisporpoylebenzene(s) and mixtures thereof.

For example, a typical FCC light olefin stream possesses the following composition as shown in Table 1:

TABLE 1

|  | Wt. % | Mol. % |
| --- | --- | --- |
| Ethane | 3.3 | 5.1 |
| Ethylene | 0.7 | 1.2 |
| Propane | 14.5 | 15.3 |
| Propylene | 42.5 | 46.8 |
| Isobutane | 12.9 | 10.3 |
| n-butane | 3.3 | 2.6 |
| Butenes | 22.1 | 18.32 |
| Pentanes | 0.7 | 0.4 |

Alkylation and/or Transalkylation Conditions

In one or more embodiments, the alkylation and/or transalkylation processes of this invention are conducted such that the organic reactants, i.e., the alkylatable aromatic compound and the alkylating agent, are brought into contact with an alkylation or transalkylation catalyst or guard bed material in a suitable alkylation or transalkylation reaction zone. Similarly, in the method for removing impurities from a hydrocarbon stream of this invention is conducted such that the organic reactants, i.e., feed stream comprising one or more hydrocarbons and undesirable impurities, are brought into contact with the guard bed material in a suitable guard bed zone. Such reaction or guard bed zones may be, for example, a flow reactor containing a fixed bed of the alkylation and/or transalkylation catalysts and/or guard bed material, under effective and suitable alkylation and/or transalkylation conditions or treatment conditions.

Such alkylation conditions can include or comprises at least one of the following: a temperature of from about 10° C. and about 400° C., or from about 10° C. to about 200° C., or from about 150° C. to about 300° C., a pressure up to about 25000 kPa, or up to about 20000 kPa, or from about 100 kPa to about 7000 kPa, or from about 689 kPa to about 4601 kPa, a molar ratio of alkylatable aromatic compound to alkylating agent of from about 0.1:1 to about 50:1, preferably from about 0.5:1 to 10:1, and a feed weight hourly space velocity (WHSV) of between about 0.1 $hr^{-1}$ and about 100 $hr^{-1}$, or from about 0.5 $hr^{-1}$ to 50 $hr^{-1}$, or from about 10 $hr^{-1}$ to about 100 $hr^{-1}$.

The reactants can be in either the vapor phase or in the liquid phase, or in the at least partially liquid phase. In one or more embodiments, the reactants can be neat, i.e., free from intentional admixture or dilution with other material, or they can include carrier gases or diluents such as, for example, hydrogen or nitrogen.

When benzene is alkylated with ethylene to produce ethylbenzene, the alkylation reaction may be carried out under at least partially liquid phase conditions including a temperature between about 150° C. and 300° C., or between about 200° C. and 260° C., a pressure up to about 20000 kPa, preferably from about 200 kPa to about 5600 kPa, a WHSV of from about 0.1 $hr^{-1}$ to about 50 $hr^{-1}$, or from about 1 $hr^{-1}$ and about 10 $hr^{-1}$ based on the ethylene feed, and a ratio of the benzene to the ethylene in the alkylation reactor from 1:1 molar to 30:1 molar, preferably from about 1:1 molar to 10:1 molar.

When benzene is alkylated with propylene to produce cumene, the reaction may be carried out under at least partially liquid phase conditions including a temperature of up to about 250° C., preferably from about 10° C. to about 200° C.; a pressure up to about 25000 kPa, preferably from about 100 kPa to about 3000 kPa; and a WHSV of from about 1 $hr^{-1}$ to about 250 $hr^{-1}$, preferably from 5 $hr^{-1}$ to 50 $hr^{-1}$, preferably from about 5 $hr^{-1}$ to about 10 $hr^{-1}$ based on the ethylene feed.

Such transalkylation conditions can include or comprises at least one of the following: a temperature of about 100° C. to about 300° C., or from about 100° C. to about 275° C., a pressure of about 200 kPa to about 600 kPa, or about 200 kPa to about 500 kPa, a weight hourly space velocity (WHSV) based on the total feed of about 0.5 $hr^{-1}$ to about 100 $hr^{-1}$ on total feed, and aromatic/poly-alkylated aromatic compound weight ratio 1:1 to 6:1.

When the poly-alkylated aromatic compounds are polyethylbenzenes and are reacted with benzene to produce ethylbenzene, the transalkylation conditions include or comprises a temperature of from about 220° C. to about 260° C., a pressure of from about 300 kPa to about 400 kPa, weight hourly space velocity of 2 to 6 on total feed and benzene/PEB weight ratio 2:1 to 6:1.

When the poly-alkylated aromatic compounds are polyisopropylbenzenes (PIPBs) and are reacted with benzene to produce cumene, the transalkylation conditions include or comprises a temperature of from about 100° C. to about 200° C., a pressure of from about 300 kPa to about 400 kPa, a weight hourly space velocity of 1 to 10 on total feed and benzene/PIPB weight ratio 1:1 to 6:1.

EXAMPLES

The invention will now be more particularly described with reference to the following Examples. Numerous modifications and variations are possible and it is to be understood that within the scope of the appended claims, the invention may be practiced otherwise than as specifically described herein.

EXPERIMENTAL

Surface Area

The surface area of a material or catalyst composition herein was determined by mercury intrusion tests performed in accordance with ASTM method D4284.

Example 1

Synthesis of Alumina-Bound MWW Framework Catalyst Compositions

Eighty (80) parts of MCM-49 crystal (an MWW framework material) were combined with 20 parts of pseudoboehmite alumina, on a calcined dry weight basis, or 65 parts of MCM-49 crystal were combined with 35 parts pseudoboehmite alumina, on a calcined dry weight basis. The pseudoboehmite alumina sources were: VERSAL-300™, obtainable from Honeywell UOP; PURAL SB™ and PURAL SB-1™, obtainable from Sasol North America Inc.; CATAPAL C1™, obtainable from Honeywell UOP; and ALUMAX PB950™, obtainable from PIDC. The MCM-49 crystal and pseudoboehmite alumina dry powder were placed in a muller or a mixer and mixed for about 10 to 30 minutes. Sufficient water was added to the MCM-49 crystal and alumina during the mixing process to produce an extrudable paste. The extrudable paste was formed into a 1/20 inch quadrulobe extrudate using an extruder. After extrusion, the 1/20th inch quadrulobe extrudate was dried at a temperature ranging from 250° F. (121° C.) to 325° F. (163° C.). After drying, the dried extrudate was heated to 1000° F. (538° C.) under flowing nitrogen. The extrudate was then cooled to ambient temperature and humidified with saturated air or steam. After the humidification, the extrudate was ion exchanged with 0.5 N to 1 N of an ammonium nitrate solution. The ammonium nitrate solution ion exchange was repeated. The ammonium nitrate exchanged extrudate was then washed with deionized water to remove residual nitrate prior to calcination in air. After washing the wet extrudate, it was dried. The dried extrudate was then calcined in a nitrogen/air mixture to a temperature of 1000° F. (538° C.) to form the alumina-bound MWW framework catalyst compositions.

Example 2

Synthesis of Silica-Bound Catalyst Compositions

Eighty (80) parts MCM-49 crystal were combined with 10 parts colloidal silica or 10 parts precipitated silica, on a calcined dry weight basis. The colloidal silica source was: LUDOX™ silica, SiO2, obtainable from Sigma-Aldrich. The precipitated silica source was: ULTRASIL™, obtainable from Evonik™. The MCM-49 and silica's were placed in a muller or mixer and mixed for about 5 to 30 minutes. Sufficient water was added to the MCM-49 and alumina during the mixing process to produce an extrudable paste. The extrudable paste was formed into a 1/20 inch quadrulobe extrudate using an extruder. After extrusion, the 1/20th inch quadrulobe extrudate was dried at a temperature ranging from 250° F. (121° C.) to 325° F. (163° C.). After drying, the dried extrudate was heated to 1000° F. (538° C.) under flowing nitrogen. The extrudate was then cooled to ambient temperature and humidified with saturated air or steam. After the humidification, the extrudate was ion exchanged with 0.5 to 1 N ammonium nitrate solution. The ammonium nitrate solution ion exchange was repeated. The ammonium nitrate exchanged extrudate was then washed with deionized water to remove residual nitrate prior to calcination in air. After washing the wet extrudate, it was dried. The dried extrudate was then calcined in a nitrogen/air mixture to a temperature of 1000° F. (538° C.) to form the silica-bound catalyst compositions.

Example 3

Synthesis of Amorphous Silica-Alumina-Bound Catalysts 1

Eighty (80) parts MCM-49 crystal were combined with 20 parts of amorphous precipitated silica-alumina, on a calcined dry weight basis. The sources of amorphous, precipitated silica-alumina were: SIRAL-20™ and SIRAL-95™, obtainable from Sasol North America, Inc. The MCM-49 and silica-alumina were placed in a muller or mixer and mixed for about 5 to 30 minutes. Sufficient water was added to the MCM-49 and alumina during the mixing process to produce an extrudable paste. The extrudable paste was formed into a 1/20 inch quadrulobe extrudate using an extruder. After extrusion, the 1/20th inch quadrulobe extrudate was dried at a temperature ranging from 250° F. (121° C.) to 325° F. (163° C.). After drying, the dried extrudate was heated to 1000° F. (538° C.) under flowing nitrogen. The extrudate was then cooled to ambient temperature and humidified with saturated air or steam. After the humidification, the extrudate was ion exchanged with 0.5 to 1 N ammonium nitrate solution. The ammonium nitrate solution ion exchange was repeated. The ammonium nitrate exchanged extrudate was then washed with deionized water to remove residual nitrate prior to calcination in air. After washing the wet extrudate, it was dried. The dried extrudate was then calcined in a nitrogen/air mixture to a temperature of 1000° F. (538° C.) to form the amorphous silica-alumina-bound catalyst compositions.

Example 4 to 13

Performance Evaluations

The activity and selectivity for aromatic alkylation of each catalyst compositions of Examples 1 to 3 was determined by a cumene alkylation test. The cumene alkylation test consists of loading the samples of the dried catalyst compositions into a batch reactor along with benzene. The reactor was then heated to 266° F. (130° C.) followed by the addition of propylene under an inert gas pressure of 300 psig. Samples were removed periodically for the duration of the test and analyzed with gas chromatography to determine the activity and selectivity of benzene alkylation with propylene. The catalytic activity of the catalyst was evaluated by monitoring the conversion of benzene and propylene as a function of time and determining a rate constant, k, which was $10^3$ times the rate constant in units of cc $gmol^{-1}$ $hr^{-1}$. The selectivity to di-isopropylbenzene (DIPB) of the catalyst was determined by calculating the ratio of DIPB to cumene (isopropylbenzene) production. Thus, a lower selectivity to DIPB represents a more mono-selective alkylation catalyst which produces a lower amount of DIPB. These catalytic activity and selectivity data were normalized based on the 80/20 VERSAL-300™ $Al_2O_3$/MCM-49 data.

Tables 2A and 2B, below, show that the catalyst composition comprised of a MWW framework material (MCM-49) bound with PURAL SB-1™ has the highest mono-selectivity for cumene alkylation compared to both other catalyst compositions of a MWW framework material bound with pseudoboehmite alumina as well as the amorphous silica and amorphous, precipitated silica-alumina binders. The catalyst composition comprised of MWW framework material (MCM-49) bound with SIRAL-95™ (which comprises 95% Si and 5% Al) has significantly lower mono-selectivities to cumene, as represented by their higher ratio of DIPB to cumene (isopropylbenzene) ratio. In addition, decreasing the crystal to binder ratio from 80/20 to 65/35 also increased the mono-selectivity of propylene alkylation for both the VERSAL-300™ and PURAL SB-1™ pseudoboehemite aluminas.

TABLE 2A

| Ex. | Binder Type | MCM-49 Crystal:BinderRatio | Normalized Rate Constant, k | Normalized DIPB/IPB Selectivity |
|---|---|---|---|---|
| 5 | VERSAL-300 ™ ($Al_2O_3$) | 65/35 | 1.0 | 1.0 |
| 6 | ALUMAX PB950 ™ ($Al_2O_3$) | 65/35 | 0.32 | 0.85 |
| 10 | PURAL SB-1 ™ ($Al_2O_3$) | 65/35 | 0.95 | 0.79 |

TABLE 2B

| Ex. | Binder Type | MCM-49 Crystal:Binder Ratio (Weight basis) | Normalized Rate Constant, k | Normalized DIPB/IPB Selectivity |
|---|---|---|---|---|
| 4 | VERSAL-300 ™ ($Al_2O_3$) | 80/20 | 1.0 | 1.0 |
| 7 | CATAPAL C1 ™ ($Al_2O_3$) | 80/20 | 1.60 | 0.95 |
| 8 | PURAL SB ™ ($Al_2O_3$) | 80/20 | 1.35 | 0.90 |
| 9 | PURAL SB-1 ™ $Al_2O_3$ | 80/20 | 1.03 | 0.83 |
| 11 | SIRAL-20 ™ (20% Si/80% Al) | 80/20 | 1.38 | 0.85 |
| 12 | SIRAL-95 ™ (95% Si/5% Al) | 80/20 | 1.15 | 1.40 |
| 13 | ULTRASIL ™ or LUDOX ™ ($SiO_2$) | 80/20 | 1.81 | 1.50 |

Example 14

Binder Physical Properties

The typical physical properties of PURAL SB-1™ and CATAPAL C1™ aluminas, discussed above, are set forth in the Table 3, below. The PURAL SB-1™ and CATAPAL C1™ have a larger particle size and a lower surface area than the VERSAL-300™ binder. In addition, the larger particle size of PURAL SB-1™ and CATAPAL C1™ aluminas have a higher selectivity to the mono-alkylated product (as evidenced by the lower normalized DIPB selectivity values in Table 2A and 2B). Not to be bound by any theory, it is believed that the lower surface area, large particle size, and lower pore volume in combination are all likely to contribute to the decrease in the diffusion length for the mono-alkylated products allowing them to be removed from the extrudate pores without subsequent alkylation to undesired heavier products.

TABLE 3

| | VERSAL-300 ™ $Al_2O_3$ | PURAL SB-1 ™ $Al_2O_3$ | CATAPAL C1 ™ $Al_2O_3$ | ALUMAX PB950 ™ $Al_2O_3$ |
|---|---|---|---|---|
| Surface Area ($m^2/g$)* | 300 | 250 | 230 | 250 |
| Particle Size $d_{50}$ (μm) | 20 | 45 | 60 | 10 |
| Pore Volume (cc/g) | 1 | 0.5 | 0.5 | 0.4 |

*After activation at 550° C. for 3 hours.

Example 15

Mercury Intrusion Evaluation

Figure 1:
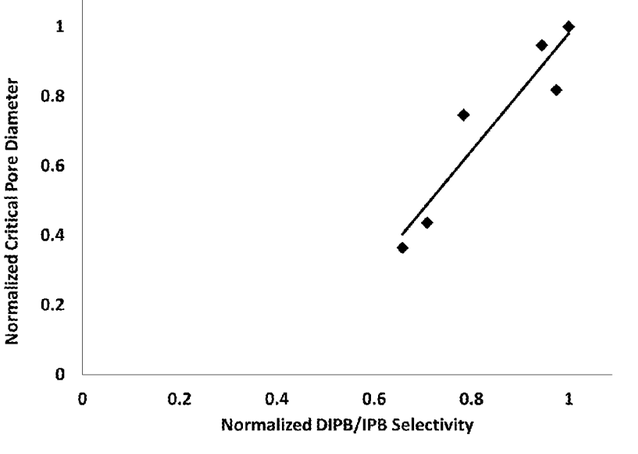
The FIGURE shows the normalized critical pore diameter as a function of the DIPB/IPB (di-isopropylbenzene/isopropylbenzene (cumene)) selectivity for the pseudoboehmite alumina-bound MWW framework catalyst compositions (i.e., MCM-49).

The pore size, pore volume, and surface area of each of the catalyst compositions of Examples 1 to 3 was determined by mercury intrusion tests performed in accordance with ASTM method D4284. These data was normalized based on the 80/20 MCM-49/VERSAL-300™ $Al_2O_3$ data. From this data, the critical pore size was determined by the inflection point of a plot of the intruded volume versus the pore diameter as determined by the mercury pressure (dV/dP) and recorded in the Table 4, below, normalized based on the 80/20 MCM-49/VERSAL-300™ $Al_2O_3$ data. The normalized critical pore diameter as a function of the DIPB/IPB (di-isopropylbenzene/isopropylbenzene (cumene)) selectivity is shown in the FIGURE for the pseudoboehmite alumina-bound MWW framework (i.e., MCM-49) catalyst compositions. A clear and unexpected trend is found as increasing alkylation mono-selectivity correlates with decreasing critical pore diameter.

TABLE 4

| Description | Normalized Critical Pore Diameter | Normalized Total Intruded Volume | Normalized Total Surface Area | Normalized DIPB/IPB Selectivity |
|---|---|---|---|---|
| 65/35 PURAL SB-1 ™/MCM-49 | 0.53 | 0.79 | 1.24 | 0.73 |
| 65/35 PURAL SB-1 ™/MCM-49 | 0.44 | 0.72 | 1.22 | 0.68 |
| 80/20 PURAL SB-1 ™/MCM-49 | 0.91 | 1.10 | 1.04 | 0.80 |
| 80/20 VERSAL-300 ™/MCM-49 | 1.16 | 1.05 | 1.69 | 0.97 |
| 80/20 VERSAL-300 ™/MCM-49 | 1 | 1 | 1 | 1 |
| 95/5 VERSAL-300 ™/MCM-49 | 1.22 | 0.86 | 0.62 | 1.03 |

Example 16

Catalyst System

The catalyst composition of this invention may be deployed in a catalyst system along with one or more another different catalysts. In a prophetic example, a catalyst system was contemplated in which the catalyst composition of this invention was deployed as a first catalyst having a higher selectivity to the mono-alkylated aromatic compound (i.e., lower selectivity for the undesirable poly-alkylated aromatic compound) but with lower catalytic activity as compared to a second catalyst composition. The second catalyst composition is located downstream of and in fluid communication with the first catalyst composition.

In such example, the catalyst system is comprised of a catalyst bed that contains 50% of the first catalyst composition in an upper portion and 50% of the second catalyst composition in the lower portion of the catalyst bed. The first and second catalyst compositions may be divided by a screen. The upper portion of the catalyst bed is disposed above and in fluid communication with the lower portion of the catalyst bed. The first catalyst composition may be any one of the catalyst compositions of inventive Examples 7 to 11 and have, for example, a zeolite content of 65% and, for example, a binder content of 35%, by weight. The second catalyst composition may be the catalyst composition of comparative Example 4 and have, for example, a zeolite content of 80% and, for example, a binder content of 20%, by weight. It is preferred that the first and second catalyst compositions have an aluminum binder. The zeolite in the first catalyst composition and/or the different second catalyst composition have a framework structure which comprises BEA*, FAU, MOR, MWW and mixtures of two or more thereof.

The alkylating agent, propylene, and the alkylatable aromatic compound, benzene, are provided to the upper portion of the catalyst bed where it is first contacted with the more selective, first catalyst composition to produce an effluent comprising the mono-alkylated and poly-alkylated aromatic compounds, along with unreacted alkylating agent and alkylatable aromatic compound. The relative selectivity to the poly-alkylated aromatic compound (DiPB/Cumene) is about 20%, and a 99% conversion of the alkylating agent is achieved at approximately 82% of the bed where the weight hourly space velocity (WHSV) is about 1 hr$^{-1}$.

Then, this effluent is then provided to the lower portion of the catalyst bed where is then contacted by the more active, second catalyst composition to produce a final effluent comprising additional mono-alkylated and poly-alkylaed aromatic compounds along with unreacted alkylatable aromatic compound and essentially no alkylating agent.

If the lower portion was operated alone, the relative selectivity to the poly-alkylated aromatic compound (DiPB/Cumene) would be about 28%, and a 99% conversion of the remaining alkylating agent would be achieved at approximately 40% of the bed where the weight hourly space velocity (WHSV) is about 2.5 hr$^{-1}$.

As can be seen, this catalyst system enables an improvement in the selectivity along with concomitant increase of the throughput (from about 1 hr$^{-1}$ up to about 2.5 hr$^{-1}$) as measured by WHSV as compared to the top bed alone.

Certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

The foregoing description of the disclosure illustrates and describes the present disclosure. Additionally, the disclosure shows and describes only the preferred embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The invention claimed is:

1. An aromatics alkylation catalyst composition for aromatics alkylation consisting of a zeolite and a mesoporous binder, said mesoporous binder is a mesoporous metal oxide which has a median particle size d$_{50}$ of greater than or equal to 20 μm and a pore volume of less than 1 cc/g, said mesoporous metal oxide has an alumina content of greater than or equal to 75%, by weight, said mesoporous metal oxide comprises amorphous silica-alumina, said zeolite has a framework structure that includes one or more of BEA* and MWW, and wherein said catalyst composition has a surface area of less than or equal to 300 m²/g as measured by ASTM D4284.

2. The aromatics alkylation catalyst composition of claim 1, wherein said framework structure includes MWW.

3. The aromatics alkylation catalyst composition of claim 1, wherein said framework structure which includes BEA* is zeolite beta, and said framework structure which includes MWW is a MCM-22 family material selected from the group consisting of MCM-22, PSH-3, SSZ-25, MCM-36, MCM-49, MCM-56, ERB-1, EMM-10, EMM-10-P, EMM-12, EMM-13, UZM-8, UZM-8HS, UZM-37, MIT-1, ITQ-1, ITQ-2, ITQ-30, and mixtures of two or more thereof.

4. The aromatics alkylation catalyst composition of claim 1, wherein said mesoporous metal oxide further comprises pseudoboehmite alumina.

5. The aromatics alkylation catalyst composition of claim 1, wherein said catalyst composition has a normalized critical pore diameter of less than 1 μm.

6. The aromatics alkylation catalyst composition of claim 1, wherein said mesoporous metal oxide has an alumina content of from 75% to 95%, by weight.

7. The aromatics alkylation catalyst composition of claim 1, wherein the ratio of said zeolite to said mesoporous metal oxide is in the range of from 1:99 to 65:35 by weight.

8. The aromatics alkylation catalyst composition of claim 1, wherein said framework structure includes said MWW, and wherein said MWW is a MCM-22 family material selected from the group consisting of EMM-10, EMM-10-P, EMM-12, EMM-13, UZM-8, UZM-8HS, UZM-37, MIT-1, ITQ-30, and mixtures of two or more thereof.

9. The aromatics alkylation catalyst composition of claim 1, wherein said framework structure includes said MWW, and wherein said MWW is a MCM-22 family material selected from the group consisting of MCM-22, MCM-49, MCM-56, and mixtures of two or more thereof.

10. The aromatics alkylation catalyst composition of claim 9, wherein the ratio of said zeolite to said mesoporous metal oxide is in the range of from 1:99 to 65:35 by weight.

11. The aromatics alkylation catalyst composition of claim 9, wherein said MCM-22 family material includes said MCM-49.

12. The aromatics alkylation catalyst composition of claim 11, wherein the pore volume of said mesoporous metal oxide is less than or equal to 0.5 cc/g.

13. The aromatics alkylation catalyst composition of claim 11, wherein the pore volume of said mesoporous metal oxide is less than or equal to 0.75 cc/g.

14. The aromatics alkylation catalyst composition of claim 1, wherein said zeolite has a constraint index of less than 1.

15. The aromatics alkylation catalyst composition of claim 1, wherein said median particle size $d_{50}$ of said mesoporous metal oxide is in a range of from 35 μm to 50 μm.

16. The aromatics alkylation catalyst composition of claim 1, wherein:
said zeolite has a constraint index of less than 1, and
the ratio of said zeolite to said mesoporous metal oxide is in the range of from 1:99 to 65:35 by weight.

17. The aromatics alkylation catalyst composition of claim 1, wherein:
the pore volume of said mesoporous metal oxide is less than or equal to 0.5 cc/g, and
said median particle size $d_{50}$ of said mesoporous metal oxide is in a range of from 35 μm to 50 μm.

18. The aromatics alkylation catalyst composition of claim 1, wherein:
the pore volume of said mesoporous metal oxide is less than or equal to 0.5 cc/g, said median particle size $d_{50}$ of said mesoporous metal oxide is in a range of from 45 μm to 50 μm, and
the ratio of said zeolite to said mesoporous metal oxide is in the range of from 1:99 to 65:35 by weight.

19. The aromatics alkylation catalyst composition of claim 1, wherein said median particle size $d_{50}$ of said mesoporous metal oxide is in a range of from 25 μm to 50 μm.

20. The aromatics alkylation catalyst composition of claim 19, wherein the amorphous silica-alumina comprises amorphous precipitated silica-alumina.

21. The aromatics alkylation catalyst composition of claim 20, wherein:
said framework structure includes said MWW, and
said MWW is a MCM-22 family material comprising one or more of MCM-22, MCM-49, and MCM-56.

22. A process for producing a mono-alkylated aromatic compound comprising the step of:
(a) contacting a portion of a stream comprising an alkylatable aromatic compound with a stream comprising an alkylating agent in the presence of an alkylation catalyst under alkylation conditions to produce an alkylation effluent which comprises said mono-alkylated aromatic compound and a poly-alkylated aromatic compound, wherein said alkylation catalyst comprises the aromatics alkylation catalyst composition of claim 1.

23. The process of claim 22, wherein:
said alkylating agent is ethylene, said mono-alkylated aromatic compound is ethylbenzene and said poly-alkylated aromatic compound is poly-ethylbenzene, or
said alkylating agent is propylene, said mono-alkylated aromatic compound is cumene and said poly-alkylated aromatic compound is poly-isopropylbenzene.

* * * * *